United States Patent
Soh et al.

(10) Patent No.: US 10,772,812 B2
(45) Date of Patent: Sep. 15, 2020

(54) HAIR CARE COMPOSITION COMPRISING NON-VOLATILE HYDROCARBON OILS AND FATTY ESTERS OF BENZOIC ACID

(71) Applicant: The Procter & Gamble Company, Cincinnati, OH (US)

(72) Inventors: Mui Siang Soh, Singapore (SG); Tian Yong Lim, Singapore (SG)

(73) Assignee: The Procter and Gamble Company, Cincinnati, OH (US)

(*) Notice: Subject to any disclaimer, the term of this patent is extended or adjusted under 35 U.S.C. 154(b) by 0 days.

(21) Appl. No.: 16/441,712

(22) Filed: Jun. 14, 2019

(65) Prior Publication Data

US 2019/0290566 A1 Sep. 26, 2019

Related U.S. Application Data

(63) Continuation of application No. PCT/US2018/033292, filed on May 18, 2018.

(60) Provisional application No. 62/508,397, filed on May 19, 2017.

(51) Int. Cl.
| | |
|---|---|
| *A61K 8/37* | (2006.01) |
| *A61K 8/31* | (2006.01) |
| *A61K 8/34* | (2006.01) |
| *A61K 8/41* | (2006.01) |
| *A61Q 5/12* | (2006.01) |
| *A61K 8/42* | (2006.01) |

(52) U.S. Cl.
CPC ............. *A61K 8/37* (2013.01); *A61K 8/31* (2013.01); *A61K 8/342* (2013.01); *A61K 8/416* (2013.01); *A61K 8/42* (2013.01); *A61Q 5/12* (2013.01); *A61K 2800/30* (2013.01); *A61K 2800/596* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 4,323,693 | A | 4/1982 | Scala, Jr. |
| 8,263,061 | B2 | 9/2012 | Olenick, Jr. |
| 2007/0071708 | A1 | 3/2007 | Ellington |
| 2016/0206547 | A1 | 7/2016 | Alves |
| 2018/0243204 | A1 | 8/2018 | Parikh |
| 2019/0290565 | A1 | 9/2019 | Soh |

FOREIGN PATENT DOCUMENTS

| | | | |
|---|---|---|---|
| CN | 103735428 | 4/2014 | |
| EP | 2565218 A1 * | 3/2013 | ............ A61K 8/898 |
| WO | WO9943838 A1 | 9/1999 | |
| WO | WO2013037752 A2 | 3/2013 | |
| WO | WO2018098542 A1 | 6/2018 | |

OTHER PUBLICATIONS

All final and non-final office actions for U.S. Appl. No. 16/441,698.
Hans-Martin Haake et al., "Determination of the substantivity of emollients to human hair", Journal of Cosmetic Science, Jul. 1, 2007, pp. 443-450.
PCT International Search Report and Written Opinion for PCT/US2018/033291 dated Aug. 24, 2018.
PCT International Search Report and Written Opinion for PCT/US2018/033292 dated Aug. 23, 2018.

* cited by examiner

*Primary Examiner* — Nannette Holloman
(74) *Attorney, Agent, or Firm* — Angela K. Haughey

(57) ABSTRACT

Disclosed is a hair care composition comprising: a cationic surfactant system; a high melting point fatty compound; a fatty ester of benzoic acid; a non-volatile hydrocarbon oil; and an aqueous carrier. The compositions of the present invention provide conditioning benefits, especially dry conditioning benefits, while providing improved clean feel.

1 Claim, No Drawings

HAIR CARE COMPOSITION COMPRISING NON-VOLATILE HYDROCARBON OILS AND FATTY ESTERS OF BENZOIC ACID

FIELD OF THE INVENTION

The present invention relates to a hair care composition comprising: a cationic surfactant system; a high melting point fatty compound; a fatty ester of benzoic acid; a non-volatile hydrocarbon oil; and an aqueous carrier. The compositions of the present invention provide conditioning benefits, especially dry conditioning benefits, while providing improved clean feel.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits.

For example, Chinese Patent Application Publication No. 103735428 A discloses a keratin conditioner which is said to be useful for restoring hair smoothness and hair damage, and discloses a composition comprising: 4-7 wt. % cetearyl alcohol, 1-2 wt. % behenyl trimethyl ammonium chloride, 1-3 wt. % cetyl trimethyl ammonium chloride, 0.5-1 wt. % 12-15 C benzoate, 1-3 wt. % cyclopentasiloxane, 0.5-1.5 wt. % dimethyl siloxane, 0.5-1 wt. % diamino siloxane.

Another example is WO 2010076484 A, which discloses an anhydrous cosmetic composition (I) comprises one or more liquid polyesters obtained by condensation of dimer and/or trimer of unsaturated fatty acid and saturated linear diol, one or more volatile oils and one or more nonvolatile oils, where the weight ratio of volatile oil/nonvolatile oil is greater than 1.5. The composition is said to provide good cosmetic properties to the hair, preferably good brightness to the hair without greasy or sticky effect. This WO publication also discloses a composition comprising (in wt. %); 10% of ethanol; 5% of 12-15 C alcohol benzoate; and 80% of isododecane.

There still exists a need for such hair care compositions, to provide conditioning benefits, especially dry conditioning benefits, while providing improved clean feel.

None of the existing art provides all of the advantages and benefits of the present invention.

SUMMARY OF THE INVENTION

The present invention is directed to a hair care composition comprising by weight:
(a) from about 0.1% to about 10% of a cationic surfactant system;
(b) from about 0.1% to about 20% of a high melting point fatty compound;
(c) from about 0.1% to about 15% of a fatty ester of benzoic acid;
(d) from about 0.1% to about 15% of a non-volatile hydrocarbon oils; and
(e) an aqueous carrier.

The compositions of the present invention provide conditioning benefits, especially dry conditioning benefits, while providing improved clean feel. Dry conditioning benefits herein are, for example, reduced hair volume as hair alignment, and/or reduced friction. Clean feel herein are, for example, reduced greasy, tacky, and/or sticky feel, reduced coated feel, and/or more free-flowing.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated.

Composition

The composition comprises: a cationic surfactant system; a high melting point fatty compound; a fatty ester of benzoic acid; a non-volatile hydrocarbon oil; and an aqueous carrier.

These ingredients, as well as the gel matrix formed by some of these ingredients, are explained below in detail.

The composition of the present invention is, preferably, substantially free of anionic surfactants in view of avoiding undesirable interaction with cationic surfactants and/or in view of stability of the gel matrix. In the present invention, "the composition being substantially free of anionic surfactants" means that: the composition is free of anionic surfactants; or, if the composition contains anionic surfactants, the level of such anionic surfactants is very low. In the present invention, the total level of such anionic surfactants is, if included, 1% or less, preferably 0.5% or less, more preferably 0.1% or less, still more preferably 0% by weight of the composition.

Cationic Surfactant System

The composition of the present invention comprises a cationic surfactant system. The cationic surfactant system can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt. More preferably, the cationic surfactant system is a mixture of mono-long alkyl quaternized ammonium salt and di-long alkyl quaternized ammonium salt.

The cationic surfactant system is included in the composition at a level by weight of preferably from about 0.1% to about 10%, more preferably from about 0.5% to about 8%, still more preferably from about 0.8% to about 5%, even more preferably from about 1.0% to about 4%.

Mono-Long Alkyl Quaternized Ammonium Salt

The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as L-glutamic acid, lactic acid, hydrochloric acid, malic acid, succinic acid, acetic acid, fumaric acid, tartaric acid, citric acid, L-glutamic hydrochloride, maleic acid, and mixtures thereof; more preferably L-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

High Melting Point Fatty Compound

The composition of the present invention comprises a high melting point fatty compound. The high melting point fatty compound is included in the composition at a level of preferably from about 0.1% to about 20%, more preferably from about 1% to about 15%, still more preferably from about 1.5% to about 8% by weight of the composition, in view of providing improved conditioning benefits such as slippery feel during the application to wet hair, softness and moisturized feel on dry hair.

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Aqueous Carrier

The conditioning composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 95% water.

Gel Matrix

The composition of the present invention comprises a gel matrix. The gel matrix comprises a cationic surfactant, a high melting point fatty compound, and an aqueous carrier.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

Fatty Esters of Benzoic Acid

The composition of the present invention comprises a fatty ester of benzoic acid.

Such fatty esters of benzoic acid are included at a level by weight of the composition of, preferably from about 0.1% to about 15%, more preferably from about 0.5% to about 10%, still more preferably from about 0.5% to about 8%, even more preferably from about 0.5% to about 6%, in view of providing clean feel.

Such fatty esters of benzoic acid useful herein are preferably those having a fatty chain of from about 4 to about 22 carbon atoms, more preferably from about 8 to about 20 carbon atoms, still more preferably from about 12 to about 15 carbon atoms, in view of providing clean feel, and can be straight or branched, saturated or unsaturated, having OH group or not. Such fatty esters of benzoic acid useful herein are preferably straight saturated alkyl benzoate without OH group.

The weight ratio of the benzoate to the non-volatile hydrocarbons is preferably from about 10:1 to 1:10, more preferably from about 8:1 to 1:8, still more preferably from about 6:1 to 1:6, in view of providing clean feel especially reduced coated feel.

Non-Volatile Hydrocarbon Oil

The composition of the present invention comprises non-volatile hydrocarbon oils.

Such non-volatile hydrocarbon oils are included at a level by weight of the composition of, preferably from about 0.1% to about 15%, more preferably from about 0.5% to about 12%, still more preferably from about 0.5% to about 10%, even more preferably from about 0.5% to about 8%, in view of providing conditioning benefits, especially dry conditioning benefits.

Such non-volatile hydrocarbon oils useful herein are preferably alkanes. Such non-volatile hydrocarbon oils useful herein are preferably those having from about 8 to about 30 carbon atoms, more preferably from about 10 to about 25 carbon atoms, still more preferably from about 15 to about 21 carbon atoms in view of providing conditioning benefit while providing clean feel especially free-flowing. Such non-volatile hydrocarbon oils useful herein are preferably those having a viscosity of from about 3 mPa·s to about 20 mPa·s, more preferably from about 4 mPa·s to about 18 mPa·s, still more preferably from about 8 mPa·s to about 14 mPa·s at 20° C., in view of providing conditioning benefit, while providing clean feel especially free-flowing to hair and improved spreadability of the composition.

In one preferred embodiment, the composition of the present invention comprises a first non-volatile hydrocarbon oil and a second non-volatile hydrocarbons. The first non-volatile hydrocarbon oils are those having smaller number of carbon atoms and lower viscosity, and the second non-volatile hydrocarbon oils are those having larger number of carbon atoms and higher viscosity. Commercially available example of such first non-volatile hydrocarbon oils is Emogreen L19 which is C15-19 alkane having a viscosity of about 9 mPa·s at 20° C. Commercially available example of such second non-volatile hydrocarbon oils is Emosmart V21, which is C18-21 alkane having a viscosity of about 13.5 mPa·s at 20° C.

The weight ratio of the first non-volatile hydrocarbons to the second non-volatile hydrocarbons is preferably from about 10:1 to 1:10, more preferably from about 5:1 to 1:5, still more preferably from about 3:1 to 1:3, in view of providing improved spreadability of the composition.

Silicone Compound

The compositions of the present invention may contain silicone compounds, for example, at a level of preferably from about 0.05% to about 10%, more preferably from about 0.1% to about 5%.

Such silicones compounds can be, for example, volatile silicones such as cyclic silicones, dimethylpolysiloxane fluid, dimethylpolysiloxane gum, silicone copolyol, amino silicone with or without polyoxyalkylene groups, and quaternized aminosilicone with or without polyoxyalkylene groups.

Other Silicones

The compositions of the present invention may additionally contain other silicones than the above described silicone compounds, for example, at a level of preferably from about 0.05% to about 10%, more preferably from about 0.1% to about 5%.

Such other silicones can be, for example, volatile silicones such as cyclic silicones, dimethylpolysiloxane fluid, dimethylpolysiloxane gum, amino silicone, and silicone copolyol. Preferred aminosilicones include, for example, those which conform to the general formula (I):

wherein G is hydrogen, phenyl, hydroxy, or $C_1C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $C_qH_{2q}L$, wherein q is an integer having a value from 2 to 8 and L is selected from the following groups: $N(R_2)CH_2CH_2N(R_2)_2$; $N(R_2)_2$; $N(R_2)_3A^-$; $N(R_2)CH_2CH_2NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is —$N(CH_3)_2$ or —$NH_2$, more preferably —$NH_2$. Another highly preferred amino silicones are those corresponding to formula (I) wherein m=0, a=1, q=3, G=methyl, n is preferably from about 400 to about 600, more preferably about 500; and L is —$N(CH_3)_2$ or —$NH_2$, more preferably —$NH_2$. Such highly preferred amino silicones can be called as terminal aminosilicones, as one or both ends of the silicone chain are terminated by nitrogen containing group.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetra-acetate; and ultraviolet and infrared screening and absorbing agents such as octyl salicylate.

Product Forms

The conditioning compositions of the present invention can be in the form of rinse-off products or leave-on products, and can be formulated in a wide variety of product forms, including but not limited to creams, gels, emulsions, mousses and sprays.

The conditioning composition of the present invention is especially suitable for rinse-off hair conditioner. Such compositions are preferably used by following steps:
(i) after shampooing hair, applying to the hair an effective amount of the conditioning compositions for conditioning the hair; and
(ii) then rinsing the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Compositions (wt %)

| Components | Ex. 1 | Ex. 2 | Ex. 3 | CEx. i | CEx. ii | CEx. iii | CEx. iv |
|---|---|---|---|---|---|---|---|
| Behenyl trimethylammonium methosulfate | 3 | — | 2.2 | 3 | 3 | 3 | 3 |

-continued

| Components | Ex. 1 | Ex. 2 | Ex. 3 | CEx. i | CEx. ii | CEx. iii | CEx. iv |
|---|---|---|---|---|---|---|---|
| Stearamidopropyl Dimethylamine | — | 3.2 | — | — | — | — | — |
| Dicetyldimonium Chloride | — | — | 0.7 | — | — | — | — |
| L-Glutamic acid | — | 1.0 | — | — | — | — | — |
| Cetyl alcohol | 1.2 | 4.3 | 1.2 | 1.2 | 1.2 | 1.2 | 1.2 |
| Stearyl alcohol | 2.9 | 3 | 3 | 2.9 | 2.9 | 2.9 | 2.9 |
| Preservatives | 0.5 | 0.5 | 0.5 | 0.5 | 0.5 | 0.5 | 0.5 |
| C12-15 alkyl benzoate | 2 | 2 | 2 | — | 2 | — | — |
| First non-volatile hydrocarbon oil *1 | 2 | 2 | 2 | — | — | 2 | — |
| Second non-volatile hydrocarbon oil *2 | 2 | 2 | 2 | — | — | — | 2 |
| Perfume | 0.6 | 0.6 | 0.6 | 0.6 | 0.6 | 0.6 | 0.6 |
| Deionized Water | q.s. to 100% of the composition | | | | | | |
| Volume reduction | About 13.8% reduction of volume, compared to C1 | — | — | C1 | About 6.6% reduction of volume, compared to C1 | About 5.2% reduction of volume, compared to C1 | About 6.5% reduction of volume, compared to C1 |
| Friction reduction | About 2.5% reduction of friction, compared to C2 | | | C2 | About 3.8% increase of friction, compared to C2 | About 2.9% increase of friction, compared to C2 | About 6.7% increase of friction, compared to C2 |

Definitions of Components
*1 First non-volatile hydrocarbon oil: Emogreen L19 which is C15-19 alkane having a viscosity of about 9 mPa · s at 20° C.
*2 Second non-volatile hydrocarbon oil: Emosmart V21, which is C18-21 alkane having a viscosity of about 13.5 mPa · s at 20° C.

Method of Preparation

The above hair care compositions of "Ex. 1" through "Ex. 3" and "CEx. i" through "CEx.iv" can be prepared by any conventional method well known in the art.

Properties and Benefits

For some of the compositions, some benefits are evaluated by the following methods. Results of the evaluation are shown above in Table.

Examples 1 through 3 are hair conditioning compositions of the present invention which are particularly useful for rinse-off use. The embodiments disclosed and represented by the previous "Ex. 1" through "Ex. 3" have many advantages. For example, they provide conditioning benefits, especially dry conditioning benefits, while providing improved clean feel. Dry conditioning benefits herein are, for example, reduced hair volume as hair alignment, and/or reduced friction. Clean feel herein are, for example, reduced greasy, tacky, and/or sticky feel, reduced coated feel, and/or more free-flowing.

Such advantages, especially dry conditioning, can be understood by the comparison between the example of the present invention (especially "Ex. 1") and comparative examples "CEx. i" and "CEx. iv"

Hair Volume (i) Preparation of Hair Switch

For the volume measurement, 15 gram hair switch with a length of 10 inch are used. The hair switches are prepared by following steps:
(1) The hair switches are bleached and combed in the same way. Then, applying 1.5 cc of non-conditioning shampoo per one hair switch, lathering, rinsing and drying the hair switches;
(2) Applying a non-conditioning shampoo at a level of 1.5 cc per one hair switch and lathering the hair switch; and rinsing the hair switch;
(3) Applying conditioner at a level of 1.5 cc per one hair switch and treating the hair switch;
(4) Rinsing the hair switch;
(5) Then drying the hair switch at 50° C. and in low humidity (30%) environment for 1.5 h; and
(6) Then placing the hair switches in a high humidity (75%) environment, for 1 h at 28° C. in which the hair switches tend to expand and increase the volume.

Hair switches are ready for volume measurements.

(ii) Volume Measurements

Volume are measured by a method described in Canadian patent application publication No. CA2567712 A1. In more detail, the volume (mm3) is measured by conducting 3D reading by the laser scanning device.

(iii) Evaluation

The above measurement in the step (ii) are conducted on at least 3 different hair switches prepared by the step (i) per one conditioner, and then calculate an average of the volume. Reduced hair volume is considered as a result of better hair alignment.

Dry Friction

Hair friction force on dry hair is measured by an instrument named Instron Tester (Instron 5542, Instron, Inc; Canton, Mass., USA). 2 g of the composition is applied to 20 g of hair sample. After spreading the composition on the hair sample, rinsing it with warm water for 30 seconds, and the hair sample is left to dry over night. The friction force (g) between the hair surface and a pad along the hair is measured.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition comprising by weight:
   (a) from about 0.1% to about 10% of a cationic surfactant system; wherein the cationic surfactant system is selected from the group consisting of behenyl trimethylammonium methosulfate; stearamidopropyl dimethylamine, dicetyldimonium chloride and combinations thereof;
   (b) from about 0.1% to about 20% of a high melting point fatty compound; wherein the high melting point fatty compound is selected from the group consisting of stearyl alcohol, cetyl alcohol, and combinations thereof;
   (c) from about 0.1% to about 15% of a fatty ester of benzoic acid;
   (d) from about 0.1% to about 15% of a non-volatile hydrocarbon oils; and
   (e) an aqueous carrier; and
   wherein the weight ratio of the fatty esters of benzoic acid to the non-volatile hydrocarbon oils is about 2:4.

* * * * *